US011568985B2

(12) United States Patent
Moskal et al.

(10) Patent No.: US 11,568,985 B2
(45) Date of Patent: Jan. 31, 2023

(54) MEDICAL DEVICE LOCATION AUTHORIZATION

(71) Applicant: Fenwal, Inc., Lake Zurich, IL (US)

(72) Inventors: Witold Moskal, Lake Zurich, IL (US); Maciej Wroblewski, Lake Zurich, IL (US); Qing Jiang, Long Grove, IL (US)

(73) Assignee: Fenwal, Inc., Lake Zurich, IL (US)

(*) Notice: Subject to any disclaimer, the term of this patent is extended or adjusted under 35 U.S.C. 154(b) by 179 days.

(21) Appl. No.: 17/081,755

(22) Filed: Oct. 27, 2020

(65) Prior Publication Data
US 2021/0043318 A1 Feb. 11, 2021

Related U.S. Application Data

(63) Continuation of application No. 15/359,690, filed on Nov. 23, 2016, now abandoned.

(60) Provisional application No. 62/259,932, filed on Nov. 25, 2015.

(51) Int. Cl.
G06F 21/62 (2013.01)
G16H 40/63 (2018.01)
(Continued)

(52) U.S. Cl.
CPC .......... *G16H 40/63* (2018.01); *G06F 21/629* (2013.01); *G16H 20/17* (2018.01); *G16H 40/20* (2018.01);
(Continued)

(58) Field of Classification Search
CPC .......... G06F 21/629; G06F 2221/2111; G06F 2221/2141; G16H 20/17; G16H 40/20;
(Continued)

(56) References Cited

U.S. PATENT DOCUMENTS 8,768,719 B2 7/2014 Wehba et al.
9,089,642 B2 7/2015 Murphy et al.
(Continued)

OTHER PUBLICATIONS

European Patent Office, "Extended European Search Report", issued in connection with European patent application No. 16002492.3, dated Apr. 12, 2017, 9 pages.
(Continued)

Primary Examiner — Minh Dinh
(74) Attorney, Agent, or Firm — Hanley, Flight & Zimmerman, LLC

(57) ABSTRACT

Systems, methods, and apparatus for medical device management are disclosed. An example tangible computer readable storage medium includes instructions that, when executed, cause a processor to at least launch a first user interface to configure a first user group based on a first role, generate a role mapping in response to configuring the first user group based on the first association, launch a second user interface to configure the first user group based on a first deployment location, generate a location mapping in response to configuring the first user group based on the second association, generate a combined location and role mapping based on the role mapping and the location mapping, and launch a third user interface to facilitate interaction of the first user account with the medical device in response to determining whether the first user account is authorized to access the medical device based on the combined mapping.

20 Claims, 19 Drawing Sheets

(51) Int. Cl.
*G16H 40/20* (2018.01)
*G16H 20/17* (2018.01)

(52) U.S. Cl.
CPC .............. *G06F 2221/2111* (2013.01); *G06F 2221/2141* (2013.01)

(58) Field of Classification Search
CPC ...... G16H 40/63; G16H 40/67; H04L 63/101; H04L 63/102; H04L 63/104; H04L 63/105; H04L 63/107
See application file for complete search history.

(56) References Cited

U.S. PATENT DOCUMENTS

| | | | |
|---|---|---|---|
| 9,307,907 | B2 | 4/2016 | Condurso et al. |
| 9,539,383 | B2 | 1/2017 | Kohlbrecher |
| 10,042,986 | B2 | 8/2018 | Ruchti et al. |
| 10,061,899 | B2 | 8/2018 | Miller et al. |
| 10,740,436 | B2 | 8/2020 | Moskal et al. |
| 2004/0167465 | A1 | 8/2004 | Mihai et al. |
| 2004/0176984 | A1 | 9/2004 | White et al. |
| 2004/0181314 | A1 | 9/2004 | Zaleski |
| 2007/0168223 | A1 | 7/2007 | Fors et al. |
| 2008/0059237 | A1 | 3/2008 | Koren et al. |
| 2008/0154177 | A1 | 6/2008 | Moubayed et al. |
| 2009/0094682 | A1 | 4/2009 | Sage et al. |
| 2009/0157202 | A1* | 6/2009 | Roberts ............... G16H 40/67 700/90 |
| 2009/0270810 | A1 | 10/2009 | DeBelser et al. |
| 2011/0047499 | A1 | 2/2011 | Mandro et al. |
| 2011/0145903 | A1 | 6/2011 | Lillie et al. |
| 2011/0289497 | A1 | 11/2011 | Kiaie et al. |
| 2013/0104120 | A1 | 4/2013 | Arrizza et al. |
| 2013/0110538 | A1 | 5/2013 | Butterfield et al. |
| 2013/0312066 | A1 | 11/2013 | Suarez et al. |
| 2013/0312084 | A1 | 11/2013 | Tandon |
| 2014/0075492 | A1 | 3/2014 | Kapadia et al. |
| 2014/0095180 | A1 | 4/2014 | Venkat et al. |
| 2014/0180711 | A1* | 6/2014 | Kamen ............... G16H 70/40 705/2 |
| 2014/0194817 | A1 | 7/2014 | Lee et al. |
| 2014/0304773 | A1 | 10/2014 | Woods et al. |
| 2015/0141955 | A1 | 5/2015 | Ruchti et al. |
| 2015/0370973 | A1 | 12/2015 | Jones |
| 2016/0034655 | A1 | 2/2016 | Gray et al. |
| 2017/0104760 | A1 | 4/2017 | Hilemon et al. |
| 2017/0147761 | A1 | 5/2017 | Moskal et al. |
| 2017/0147771 | A1 | 5/2017 | Moskal et al. |

OTHER PUBLICATIONS

European Patent Office, "Extended European Search Report", issued in connection with European patent application No. 16002493.1, dated Apr. 11, 2017, 8 pages.

United States Patent and Trademark Office, "Non-Final Office action," issued in connection with U.S. Appl. No. 15/359,680, dated Nov. 27, 2018, 52 pages.

European Patent Application, "Communication pursuant to Article 94(3) EPC," issued in connection with European patent application No. 16 002 493.1, dated Nov. 2, 2018, 7 pages.

United States Patent and Trademark Office, "Final Office Action," dated Apr. 8, 2019 in connection with U.S. Appl. No. 15/359,680 (26 pages).

United States Patent and Trademark Office, "Non-Final Office Action," dated Aug. 7, 2019 in connection with U.S. Appl. No. 15/359,680 (18 pages).

United States Patent and Trademark Office, "Advisory Action," dated Jul. 3, 2019 in connection with U.S. Appl. No. 15/359,680 (3 pages).

European Patent Application, "Communication pursuant to Article 94(3) EPC," issued in connection with European patent application No. 16 002 492.3, dated Oct. 8, 2019, 6 pages.

United States Patent and Trademark Office, "Notice of Allowance," dated Feb. 11, 2020 in connection with U.S. Appl. No. 15/359,680 (8 pages).

United States Patent and Trademark Office, "Non-Final Office action," issued in connection with U.S. Appl. No. 15/359,690, dated Dec. 10, 2018, 17 pages.

Science Applications International Corporation (SAIC), Role-Based Access Control (RBAC) Role Engineering Process, Version 3.0, The Healthcare RBAC Task Force, May 11, 2004, 40 pages.

Elisa Bertino et al., GEO-RBAC: A Spatially Aware RBAC, ACM Transactions on Information and System Security, Jan. 2005, 40 pages.

Indrakshi Ray et al., LRBAC: A location-aware role-based access control model, Information System Security, Dec. 2006, 16 pages.

Edward Killeen, Role mapping for complete RBAC, empowerID, Sep. 11, 2012, 4 pages.

United States Patent and Trademark Office, "Final Office Action," dated May 31, 2019 in connection with U.S. Appl. No. 15/359,690 (16 pages).

Dean Wiech, "Role based acess control in Healthcare," Aug. 26, 2013, Healthcare IT News, 2 pages.

Jasmine Pennic, "Role-Based Access Control Ensures Extra Security in Healthcare," May 7, 2013, hitconsultant.net, 5 pages.

Frode Hansen and Vladimir Oleshchuk, "Application of Role-Based Access Control in Wireless Healthcare Information Systems," Mar. 2004, Agder University College, 4 pages.

United States Patent and Trademark Office, "Non-Final Office Action," dated Jan. 31, 2020 in connection with U.S. Appl. No. 15/359,690 (13 pages).

United States Patent and Trademark Office, "Final Office Action," dated Jul. 27, 2020 in connection with U.S. Appl. No. 15/359,690 (16 pages).

European Patent Office, "Summons to attend oral proceeding pursuant to Rule 115(1) EPC", issued in connection with European Patent Application No. 16002493.1, Jun. 25, 2021 (10 pages).

* cited by examiner

ROLE AND FUNCTIONALITIES MAPPING ⟵ 300

| USER ROLE | MONITOR PUMP STATUS | ABORT DATA SETS DISTRIBUTION | DATA SET DISTRIBUTION REPORT | CREATE DATA SET DISTRIBUTION POLICY | DATA SET UPLOAD | INFUSION DATA REPORTING |
|---|---|---|---|---|---|---|
| ADMINISTRATOR | Y | Y | Y | Y | Y | Y |
| BIOMEDICAL ENGINEER | Y | Y | Y | Y | N | Y |
| PHARMACIST | Y | Y | Y | Y | Y | Y |
| PHARMACY TECHNICIAN | Y | N | Y | N | N | Y |
| FRESENIUS KABI BUSINESS ANALYST | Y | Y | Y | Y | Y | Y |
| NURSE | N | N | N | N | N | Y |

FIG. 3

CONFIGURATION > ROLES

| CONFIGURATION | ORGANIZATION | HOSPITALS | ROLES | LANGUAGES |
|---|---|---|---|---|

| NAME | < USER GROUP NAME |
|---|---|
| ADMINISTRATOR | EVERYONE |
| BIOMEDICAL ENGINEER | DXTBVEO |
| FRESENIUS KABI BUSINESS ANALYST | |
| NURSE | |
| PHARMACIST | DXTPHRM |
| PHARMACY TECHNICIAN | |

CANNOT CHANGE NAME OR PARENT LOCATION OF HOSPITALS WITH ASSOCIATED DEVICES

NAME GERI_HOSPITAL B1

CORPORATION GERI_ORG1

TIME ZONE (UTC-6:00) CENTRAL TIME (US & CANADA)

DAYLIGHT SAVINGS ✓

USER GROUP NAME DXTLOC2

ADDRESS LINE 1

ADDRESS LINE 2

CITY

STATE

FIG. 12A

DEVICES > PUMPS

PUMPS

| LOCATIONS: ALL ⌄ | | DEVICE TYPE: ALL ⌄ | | FILTER BY SERIAL NUMBER | |
|---|---|---|---|---|---|
| HOSPITAL | SERIAL NUMBER⌄ | DEVICE TYPE | TARGET DATA SET | ACTIVE DATA SET | LAST CONNECTION | MAC ADR |
| GERI_HOSPITAL A1 | Z019735/10150403 | AGILIA VP MC | DOUG 2015-11-11V2-000 | DOUG 2015-11-11V2-000 | 11/17/2015 9:56 | 00:23 |
| GERI_HOSPITAL B1 | Z019735/01010101 | AGILIA VP MC | DOUG 2015-11-11V2-000 | DOUG 2015-11-11V2-000 | 11/17/2015 9:56 | 00:23 |
| GERI_HOSPITAL B1 | Z019735/10150429 | AGILIA SP MC | DOUG 2015-11-11V2-000 | DOUG 2015-11-11V2-000 | 11/10/2015 9:56 | 00:23 |

DEVICES

FIG. 12B

MEDICAL DEVICE LOCATION AUTHORIZATION

CROSS-REFERENCE TO RELATED APPLICATIONS

This patent arises from a continuation of U.S. patent application Ser. No. 15/359,690, which was filed on Nov. 23, 2016, which relates and claims priority to U.S. Provisional Patent Application No. 62/259,932, filed on Nov. 25, 2015. U.S. patent application Ser. No. 15/359,690 and U.S. Provisional Patent Application No. 62/259,932 are hereby incorporated herein by reference in their entireties. Priority to U.S. patent application Ser. No. 15/359,690 and U.S. Provisional Patent Application No. 62/259,932 are hereby claimed.

FIELD

The present disclosure relates generally to medical devices. More specifically, the present disclosure relates to methods, systems, and apparatus to provide location authorization and access control for medical devices.

BACKGROUND

Increasingly, medical devices are becoming electronic or involve an electronic or software component. Electronic devices, distributed facilities, and scattered patients make training, treatment, and troubleshooting difficult. Further, it is often difficult to educate the public, and patients may not seek the treatment they should due to a lack of information and access. Operators and administrators may also introduce inefficiencies in their operation and management of medical devices due to a lack of information and access. Additionally, unauthorized access has potential to introduce harmful error as well as inefficiency into patient treatment.

BRIEF DESCRIPTION OF SEVERAL VIEWS OF THE DRAWINGS

FIG. 3 illustrates an example mapping of user role and permitted functionality.

FIGS. 9A-9C illustrate example user interfaces to configure a user group name.

FIGS. 10A-10C illustrate example user interfaces to configure a user group name.

FIGS. 12A-12B illustrate example user interfaces for medical device monitoring.

Figure 1:
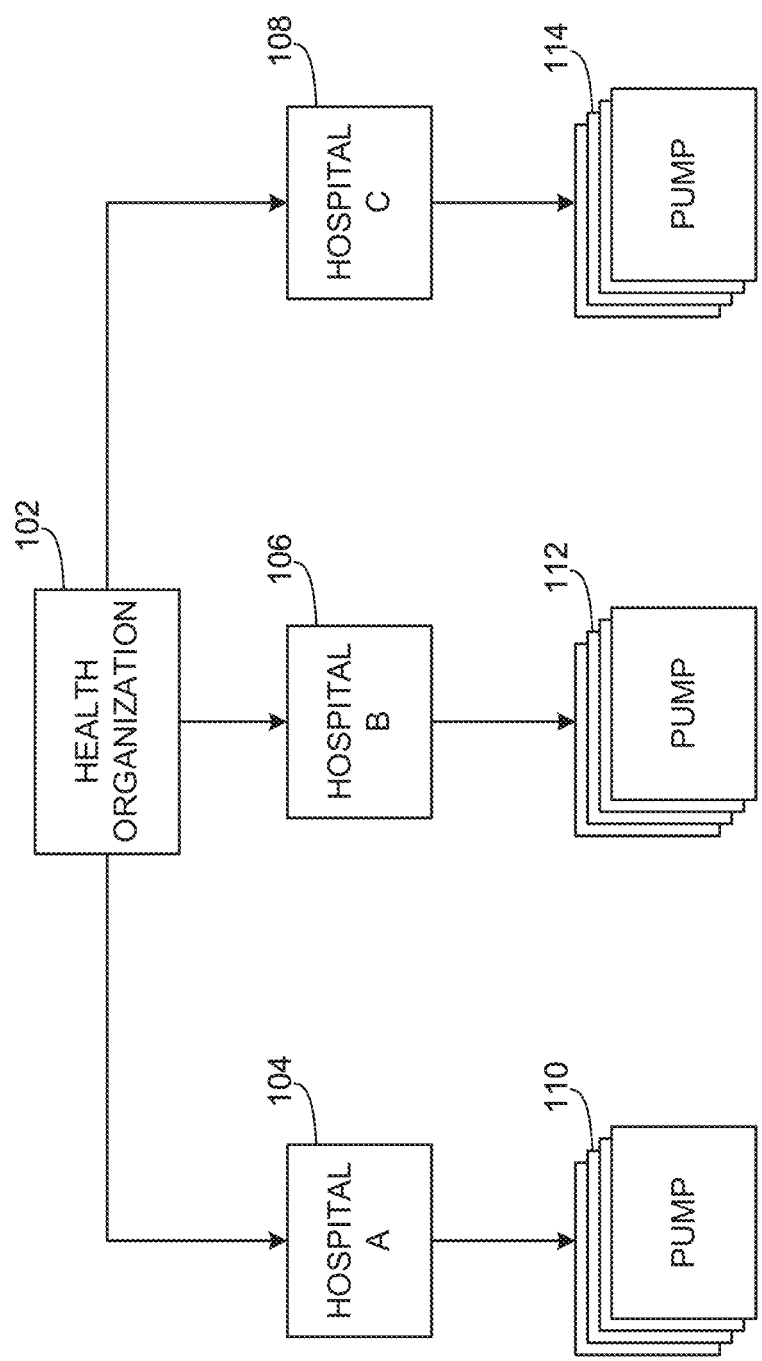
FIG. 1 illustrates an example hospital deployment location structure.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DESCRIPTION OF CERTAIN EXAMPLES

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

It will be understood that the present invention may be embodied in other specific forms without departing from the spirit thereof. The present examples and embodiments, therefore, are to be considered in all respects as illustrative and not restrictive, and the invention is not to be limited to the details presented herein.

Although the following discloses example methods, apparatus, systems, and articles of manufacture including, among other components, firmware and/or software executed on hardware, it should be noted that such methods, apparatus, systems and articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

When any of the appended claims are read to cover a purely software and/or firmware implementation, at least one of the elements is hereby expressly defined to include a tangible medium such as a memory, a digital video disc (DVD), compact disc (CD), BLU-RAY™, etc. storing the software and/or firmware.

Certain examples facilitate management of medical devices including blood collection or apheresis devices, infusion pumps, drug delivery pumps, and/or other medical devices. For example, an infusion pump infuses fluids, medication, or nutrients into a patient. An infusion pump can be used intravenously, subcutaneously, arterially, and/or epidurally, for example. For example, an infusion pump can administer injections at a variety of rates (e.g., injections too small for an intravenous (IV) drip (e.g., 0.1 mL per hour), injections per minute, injections with repeated boluses, patient-controlled injections up to maximum number per hour, or injections of fluids whose volumes vary by time of day, etc.).

In certain examples, an operator (e.g., a technician, nurse, etc.) provides input regarding type of infusion, mode, and/or other device parameter. For example, continuous infusion provides small pulses of infusion (e.g., between 500 nanoliters and 10 milliliters), with a pulse rate based on a programmed infusion speed. Intermittent infusion alternates between a high infusion rate and a low infusion rate with timing programmable to keep a cannula open, for example. Patient-controlled infusion provides on-demand infusion with a preprogrammed ceiling to avoid patient intoxication. The infusion rate is controlled by a pressure pad or button that can be activated by the patient, for example. Infusion pumps can include large volume pumps (e.g., for nutrient solution delivery to feed a patient), small-volume pumps (e.g., for medicine delivery), etc.

In certain examples, an operator or administrator may configure a medical device, such as an infusion pump, apheresis device, etc., and/or set one or more parameters for interaction between the device and a domain controller and/or a provider data management system. Certain examples provide flexibility in facilitating operator and/or administrator (e.g., user) operation and configuration of a medical device while maintaining device reliability and secure through new authorization protocols and systems.

Certain examples provide location authorization preventing a user from accessing data and performing actions in locations other than location(s) at which the user has been authorized to act. By adding location authorization to a medical device authorization protocol, a medical device data management system (such as the Fenwal DXT™ data management system manufactured by Fenwal™, a Fresenius Kabi company) provides application level end-to-end security control to protect location data, application function, patient safety, etc. User permission is assigned depending on not only a functional role of the user but also a location assignment for the user as maintained by the data management system. Thus, data management systems can interact with medical devices (e.g., Fenwal Amicus™ Alyx™ Autopheresis-C™ and Aurora™ Apheresis systems, other apheresis devices, Fresenius Kabi Agilia® pump, Optima™ pump, Pilot™ pump, other drug delivery pump, etc.) for flexible, remote configuration and operation while helping to ensure data and configuration safety and security, for example.

In certain examples, a role-based authorization mechanism defines a user type, function, or role (e.g., system engineer, technician, nurse, physician, administrator, etc.) as well as a location (e.g., a particular healthcare facility, healthcare organization, city, employer, etc.) and user (e.g., a user account or profile that associates the user with a defined role, etc.). Thus, if a user has an account and the account identifies him or her as a member of the system engineering group, then that user can access to all resources that system engineers have (pending location limitations, etc.).

Using a location authorization schema, a logical structure of a healthcare organization (e.g., a hospital deployment structure with individual pumps, etc.) is incorporated into a user authorization system so that a user is assigned a specific role (e.g., a pharmacist in hospital A in Highmountain Healthcare, a pharmacist in a particular ward, etc.) and also restricted to a specific location (e.g., all pharmacist group access but only in Hospital A, not at Hospital B or C). Thus, the location and role-based user authorization provides a greater granularity to restrict people at a location even though the users have certain privileges from their assigned roles.

FIG. 1 illustrates an example hospital deployment location structure 100 including a health organization 102 including a plurality of hospitals 104, 106, 108 under its umbrella. Each hospital A 104, B 106, and C 108 includes one or more pumps and/or other medical devices 110, 112, 114 with electronic configuration and operation ability.

The deployment location structure 100 provides information about the logical structure of the organization 102 in which a data management system (e.g., Fenwal DXT™, etc.) is installed. In certain examples, deployment locations can be categorized into the following types: Organization, Hospital, Ward, etc. In such examples, the organization location represents the overall healthcare organization 102 in which the data management system is being deployed. The hospital location represents a single hospital 104, 106, 108 that belongs to the Organization 102. In certain examples, the ward location represents a single ward location that belongs to a hospital location.

Figure 2:
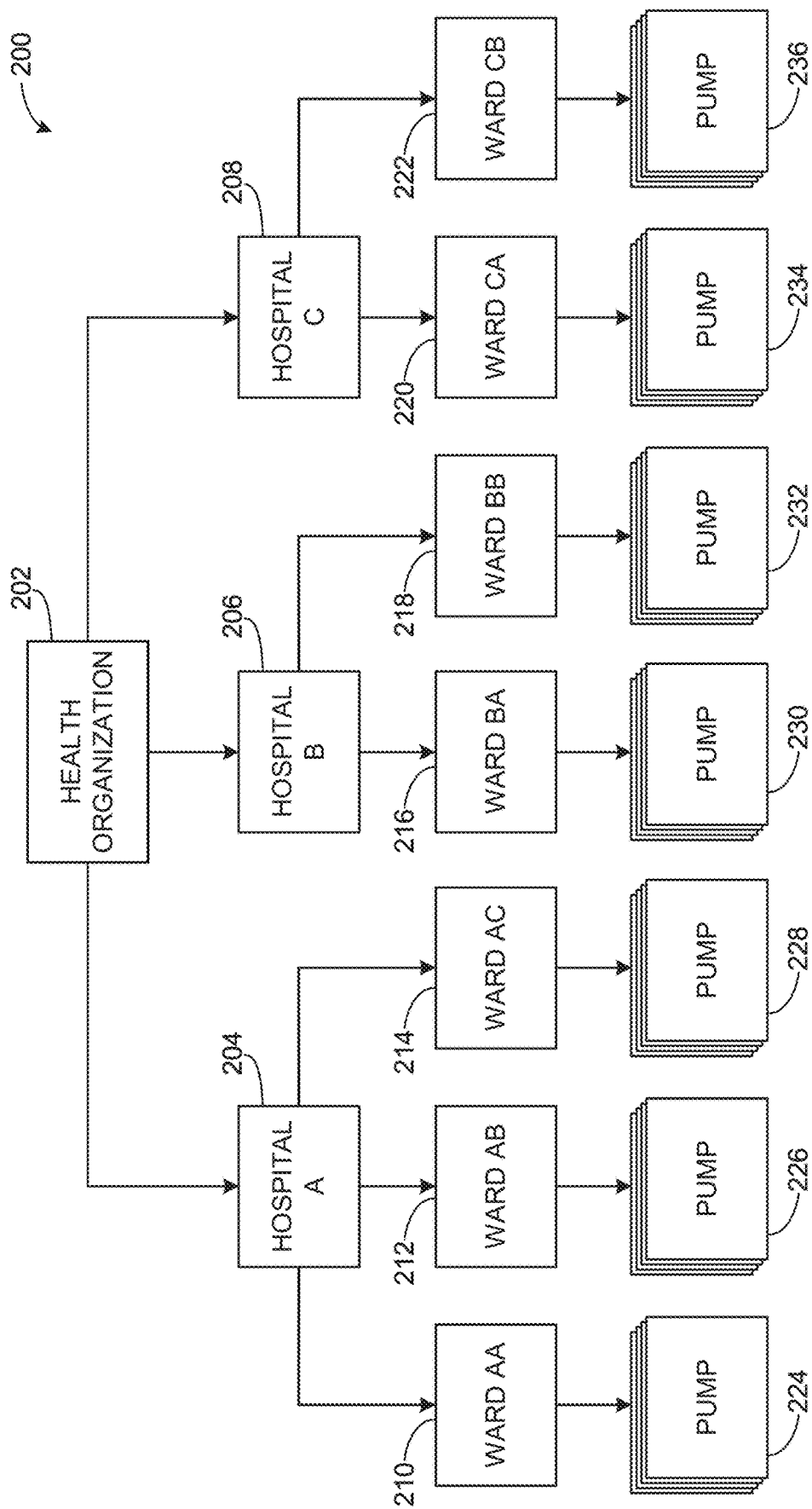
FIG. 2 illustrates an example ward deployment.

FIG. 2 illustrates an example ward deployment 200. The example ward deployment 200 of FIG. 2 includes a health organization 202 including a plurality of hospitals 204, 206, 208 under its umbrella. Each hospital A 204, B 206, and C 208 includes a plurality of wards 210-222, and each ward 210-222 includes one or more pumps and/or other medical devices 224-236 with electronic configuration and operation ability. As shown in the example of FIG. 2, health organization 202 includes Hospital A 204, Hospital B 206, and Hospital C 208. Hospital A 204 includes Ward AA 210, Ward AB 212, and Ward AC 214. Hospital B 206 includes Ward BA 216 and Ward BB 218. Hospital C 208 includes Ward CA 220 and Ward CB 222. As shown in the example of FIG. 2, each Ward 210-222 has a plurality of networked pumps 224-236 for operator configuration and operation.

FIG. 3 illustrates an example mapping 300 of user role and permitted functionality for a medical device pump example. As shown in the example of FIG. 3, user roles include administrator, biomedical engineer, pharmacist, pharmacy technician, business analyst, nurse, etc. The example of FIG. 3 also lists functionality relating to the pump device, such as monitor pump status, abort data set distribution, data set distribution report, create data set distribution policy, data set upload, infusion data reporting, etc. For each use role, the mapping 300 provides which functionality is available to a user in the particular role. Thus, as shown in the example of FIG. 3, an administrator is able to monitor pump status, abort data set distribution, view/generate a data set distribution report, create a data set distribution policy, upload a data set, view/generate an infusion data report, etc. A biomedical engineer, however, cannot upload a data set but can access the remaining functionality, while the pharmacist and business analyst are allowed access to all pump and reporting functionality in the example mapping 300. A pharmacy technician, however, is only allowed to monitor pump status, view/generate a data set distribution report, and view/generate an infusion data report, not abort data set distribution, create data set distribution policy, or upload a data set. According to the example mapping 300, a nurse may only view/generate an infusion data report.

Certain examples provide an authorization model for human users that uses Role and Location Mapping mechanisms to assign permissions to users depending on their functional role and location assignment in the system, regardless if the user accesses the data management system directly from a user interface and/or through an external system (e.g., Vigilant DrugLib, etc.). For example, when both role and location mapping have been configured, a user who wants to schedule a Dataset distribution in Hospital ABC must be authorized to be a Pharmacist who belongs to Hospital ABC location.

Certain examples provide an architecture to facilitate interaction between the data management system and a domain controller. The domain controller defines groups and users, and the data management system maps groups and users to roles and specifies locations using the domain controller information. The architecture provides and/or uses a mapping to cross-reference locations from the data management system to an active directory of the domain controller. Employees/users are assigned to certain location to prevent users from improperly accessing information and/or functionality at other locations. Assignment of a user/group for location is similar to assigning a role to a user and/or group of users as described above.

Thus, mapping dictates user interaction with a medical device (e.g., a pump, apheresis device, etc.) at a given location. For example, if a user has pharmacist privileges at one location, he or she can only distribute a drug library to the pumps at that location for which he or she has authorization.

Figure 4:
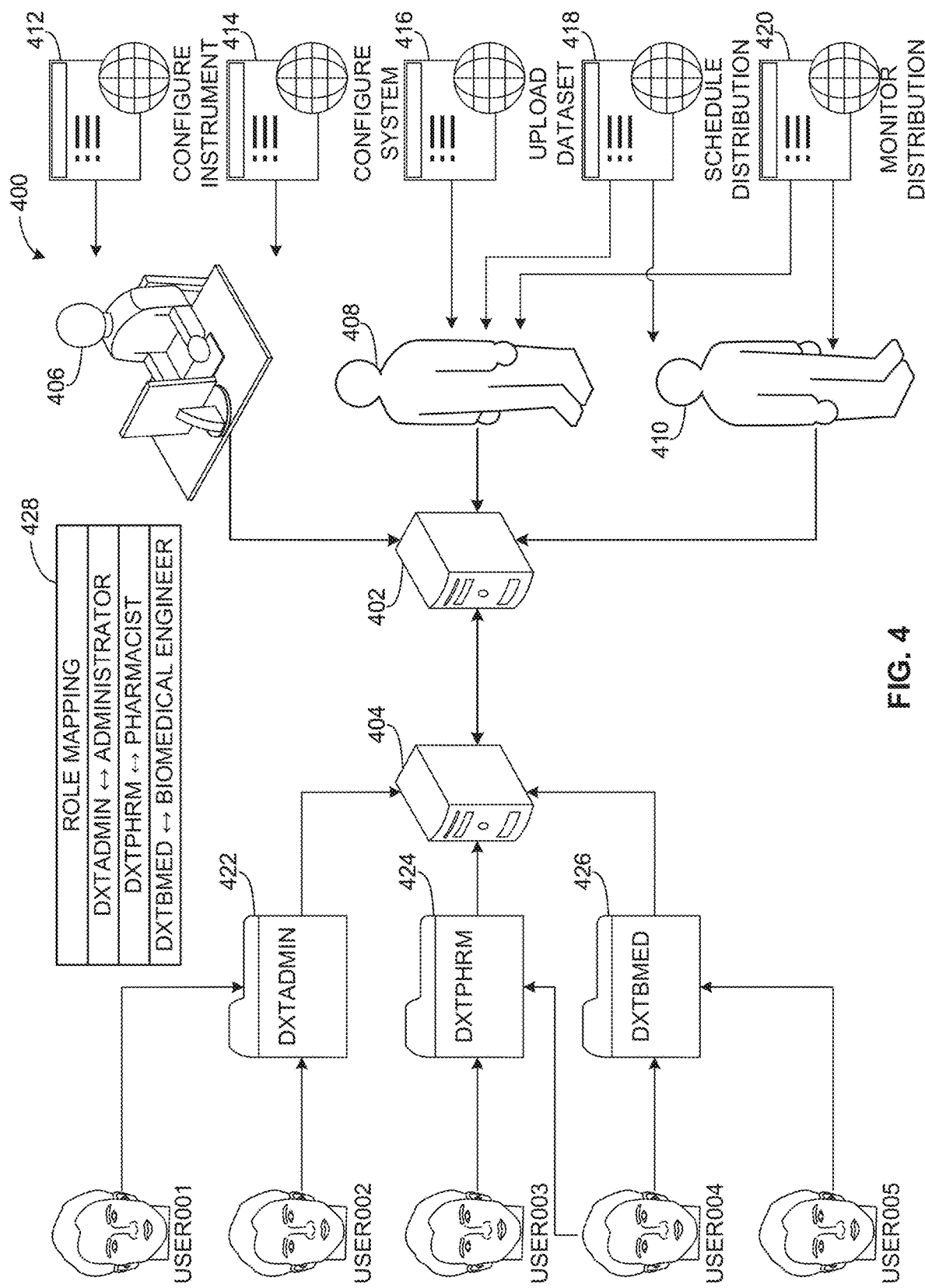
FIG. 4 illustrates an example role mapping architecture or system to configure, store, and implement a mapping of roles to user(s) and/or group(s) of users.

FIG. 4 illustrates an example role mapping architecture or system 400 to configure, store, and implement a mapping of roles to user(s) and/or group(s) of users. The role mapping architecture 400 enables an Administrator and/or automated system to configure mapping of roles provided by a data management system 402 (e.g., Pharmacist, Biomedical Engineer, Administrator, etc.) to groups of users defined within a domain controller 404 (e.g., Active Directory) of a deployment information technology (IT) infrastructure.

As shown in the example of FIG. 4, the data management system 402 defines a plurality of roles such as administrator 406, pharmacist 408, and biomedical engineer 410. Each role 406, 408, 410 is associated with one or more device functions, such as configure instrument 412, configure system 414, upload dataset 416, schedule distribution 418, monitor distribution 420, etc. For example, the administrator 406 can configure the instrument 412 and configure the system 414. The pharmacist 408 can upload a dataset 416, schedule distribution 418, and monitor distribution 420, for example. The biomedical engineer 410 can schedule distribution 418 and monitor distribution 420, for example.

The domain controller 404 defines a plurality of user groups such as an administrator user groups such as administrator group (e.g., DXTADMIN) 422, pharmacist group (e.g., DXTPHRM) 424, and biomedical group (DXTBMED) 426. One or more users are associated with each group 422, 424, 426. For example, in the example of FIG. 4, user001 and user002 are part of the administrator group 422. User003 and user004 are part of the pharmacist group 424. User004 and user005 are part of the biomedical group 426.

As illustrated in the example system 400 the role 406, 408, 410 (e.g. Administrator, Pharmacist, Biomedical Engineer, etc.) and its corresponding function permissions 412-420 are predefined by a permission roles mapping 428. For example, when the mapping 428 between domain controller DXTPHRM user group 424 and Pharmacist role 408 has been configured, any user who belongs to DXTPHRM group 424 is able to use all functions (e.g., upload dataset 416, schedule dataset distribution 418, monitor dataset distribution 420, etc.) permitted to Pharmacist role 408 by the data management system 402.

Figure 5:
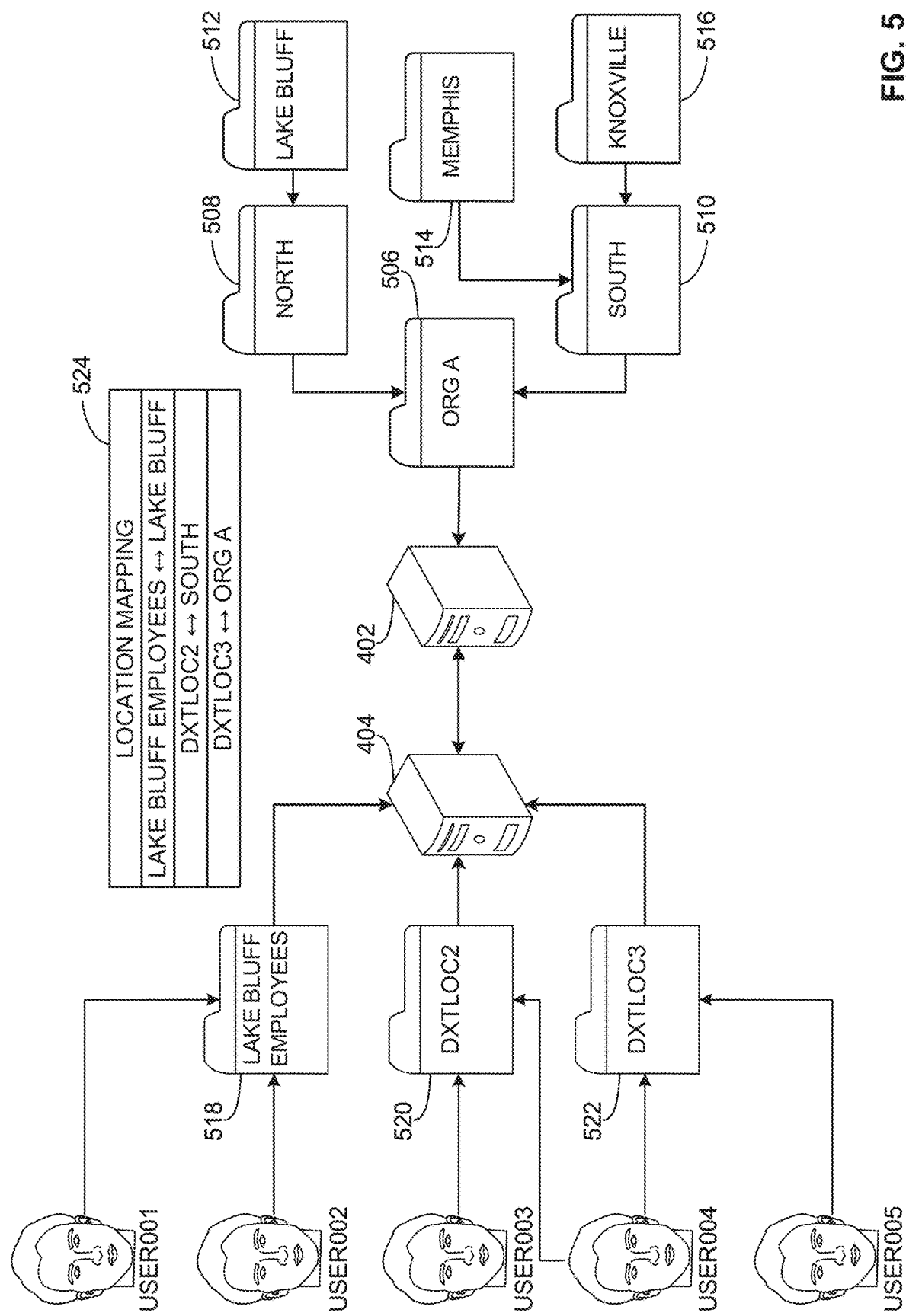
FIG. 5 illustrates an example location mapping architecture or system to configure, store, and implement a mapping of locations to user(s) and/or group(s) of users.

FIG. 5 illustrates an example location mapping architecture or system 500 to configure, store, and implement a mapping of locations to user(s) and/or group(s) of users. The location mapping architecture 500 enables an Administrator and/or automated system to configure mapping of locations defined within the data management system 402 (e.g. Lake Bluff site, Memphis site, Knoxville site, etc.) to the defined groups of users within the domain controller 404 (e.g. Active Directory) of the deployment IT infrastructure (e.g., Lake Bluff Employees, location 2 employees, location 3 employees, etc.).

For example, the data management system 402 defines and/or stores information for a plurality of facility 506 locations. In the example of FIG. 5, locations are broken up by region, such as a North region 508 and a South region 510. Within each region 508, 510 individual cities and/or other sub-regions can be identified. For example, the North region 508 for organization OrgA 506 may include a Lake Bluff location 512. The South region 510 in the example of FIG. 5 may include Memphis 514 and Knoxville 516 locations.

As shown in the example of FIG. 5, the domain controller 404 also defines and/or stores information for a plurality of user groups 518, 520, 522 by location. For example, user groups may include a Lake Bluff employees group 518, a location 2 users group (e.g., DXTLOC2) 520, a location 3 users group (e.g., DXTLOC3) 522, etc. As shown in the example of FIG. 5, user001 and user002 may belong to the Lake Bluff employees group 518; user003 and user004 belong to location 2 user group 520; and user004 and user005 belong to the location 3 user group 522. A location mapping 524 stores the relationship between user group 518, 520, 522 and location 506, 508, 510, 512, 514, 517. The mapping 524 can tie a group (e.g., Lake Bluff employees 518) to a single location (e.g., Lake Bluff), to a region (e.g., DXTLOC2 520 to South 510), and/or to an entire network (e.g., DXTLOC3 522 to OrgA 506), for example.

The locations 506-516 and their mapping 524 to domain controller groups 518-522 is defined during system configuration and, in some examples, can be updated dynamically based on changes in employment, location, rule, etc. For example, when a mapping between domain controller DXTLOC2 group 520 and DXT South location 510 has been configured, any user who belongs to DXTLOC2 group 520 can access all information for the South location 510.

Figure 6:
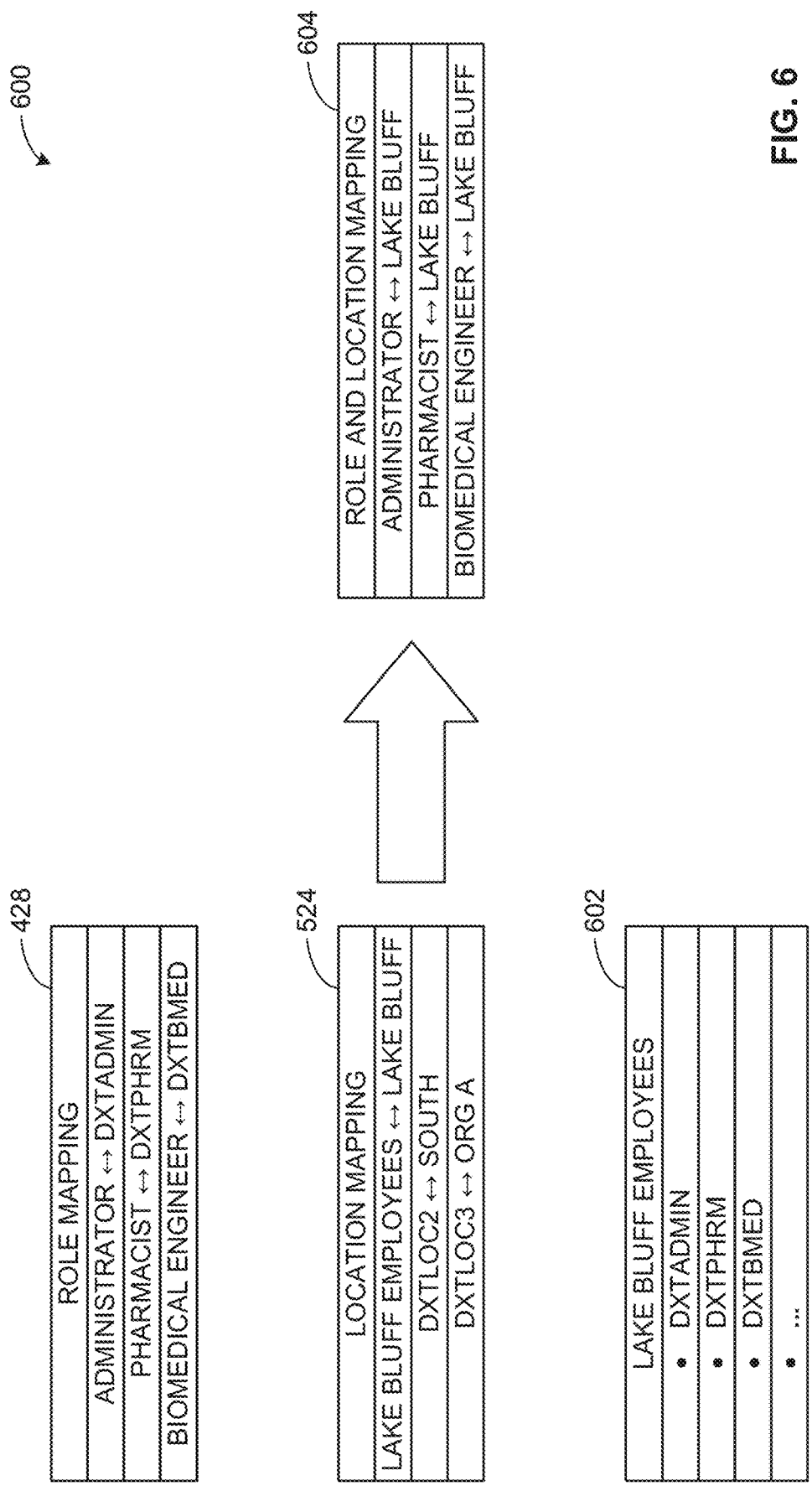
FIG. 6 illustrates an example role and location mapping schema to configure and govern user access to medical device systems at various locations.

FIG. 6 illustrates an example role and location mapping schema 600 to configure and govern user access to medical device systems at various locations. As shown in the example of FIG. 6, the role mapping 428 from the example of FIG. 4 and the location mapping 524 from the example of FIG. 5 are combined with employee information 602 from a selected group (e.g., Lake Bluff employees 518 from the example of FIG. 5) to form a role and location mapping 604. For example, the role mapping 428 provides an association between user groups and roles, as well as function(s) accessible to the roles. The location mapping 524 provides a correlation between user groups and locations. Thus, a given user has both a role and a location, and a combined role and location mapping 604 can be formed by correlating roles and locations according to an employee group list 602. Using the combined role and location mapping 604, the Administrator 406, Pharmacist 408, and Biomedical Engineer 410 can access all information and use all functions 412-420 (e.g., schedule Dataset distribution, monitor Dataset distribution, upload Dataset, configure system, configure instrument, etc.) permitted to their respective role for the Lake Bluff location 512 only.

Figure 7:
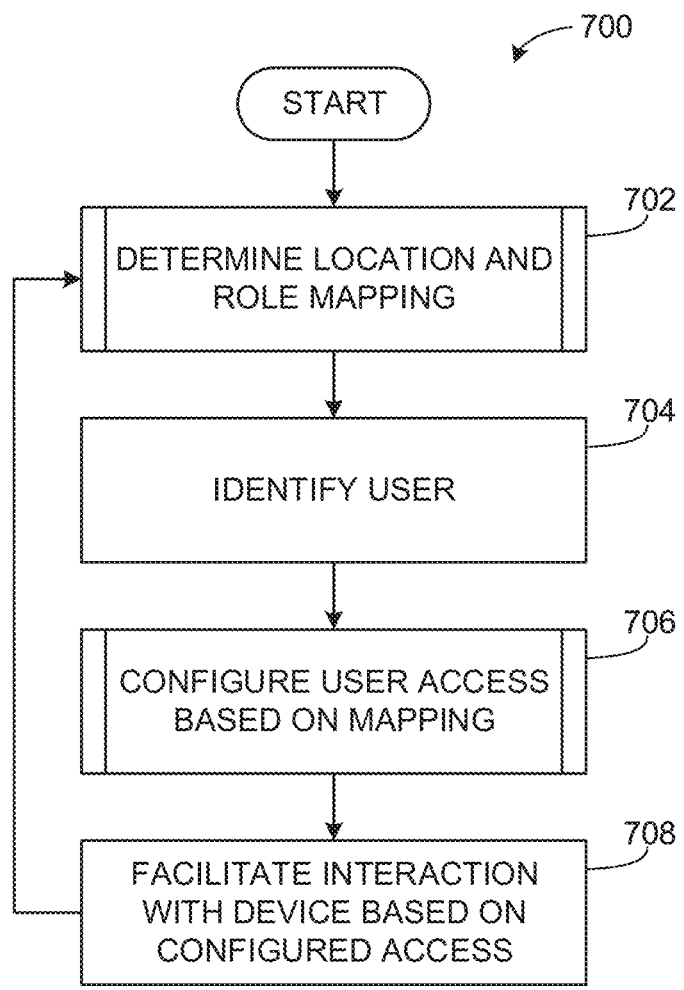
FIG. 7 illustrates a flow diagram for location and role-based authorization of action at a medical device.

FIG. 7 illustrates a flow diagram 700 for location and role-based authorization of action at a medical device. At block 702, a location and role mapping is determined. For example, as described above with respect to FIG. 4, available role(s) and associated capability(-ies) are identified and mapped to one or more users and/or user groups via the data management system 402 and domain controller 404. The role mapping 428 provides guidance to the data management system 402 to govern access to medical devices in communication with and/or controlled by the data management system 402. Additionally, as described above with respect to FIG. 5, the location mapping 524 is generated by evaluating available locations (e.g., network, region, city, etc.) and associating users and/or user groups with the available locations. The role mapping 428 and location mapping 524 are combined with employee/user information 602 to form the role and location mapping 604 for particular users having particular roles at particular locations.

At block 704, a particular user is identified. For example, a particular user logs in and is identified as a pharmacist in the pharmacy group 424 associated with the pharmacy role 408 and in the Lake Bluff employees 518 group authorized at the Lake Bluff location 512.

At block 706, the data management system 402 and domain controller 404 configure access for that user based on the mapping 604 associated with the user. For example, based on the determination of which location(s) and which function(s) the user is permitted to access based on his or her role, the data management system 402 and/or the domain controller 404 configure functionality available to the user when he or she logs in and/or otherwise accesses a medical device, user interface, workstation, etc., at a particular location.

At block 708, the data management system 402 facilitates interaction with one or more connected medical devices (e.g., infusion pump, apheresis device, etc.) based on the configured access. For example, the data management system 402 can provide the access configuration to a particular device for the specific user. The user can then interact with the medical device (e.g., the pump, the apheresis device, the workstation, etc.) according to allowed configuration for that user.

Figure 8:
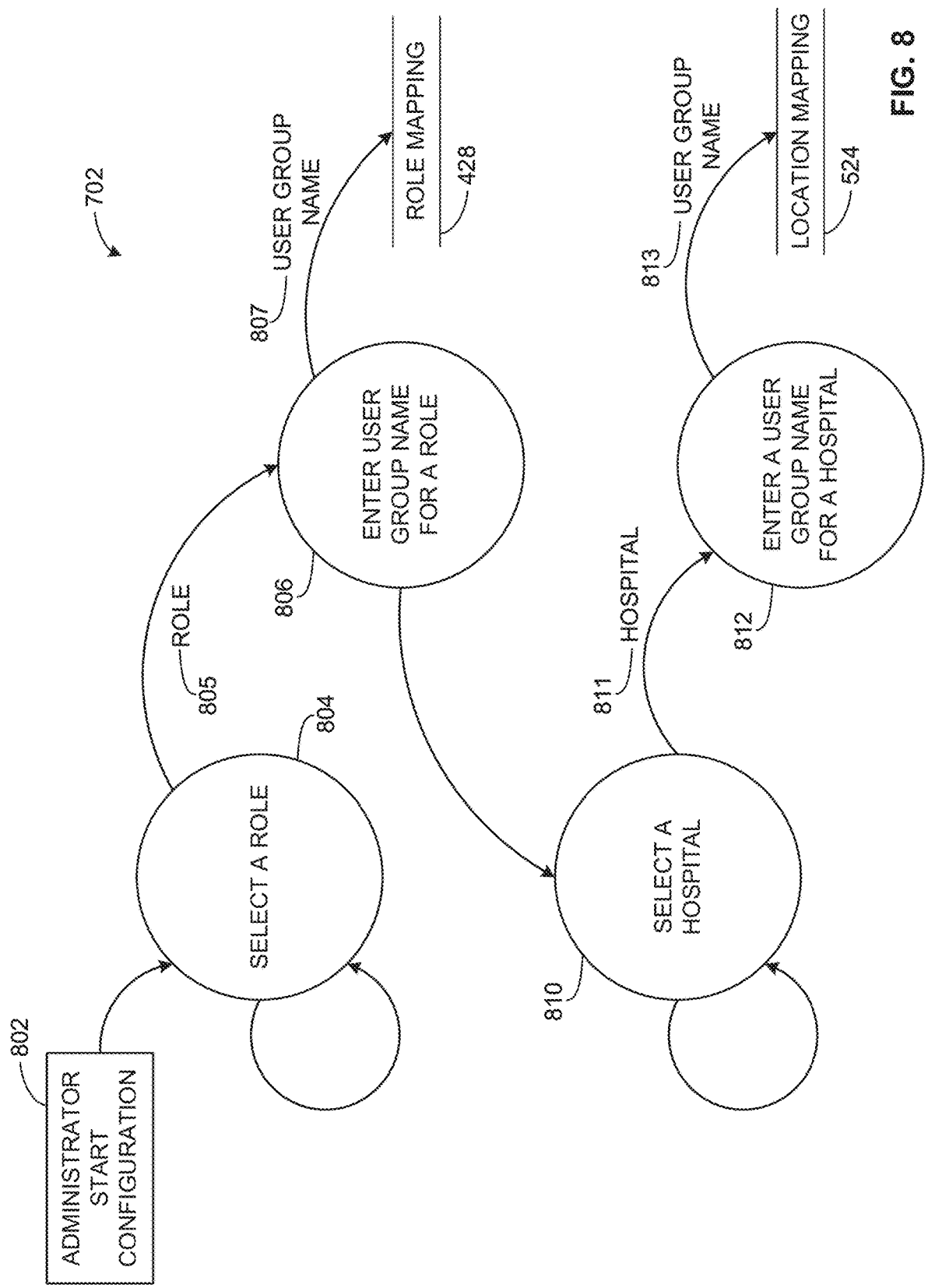
FIG. 8 depicts a data flow diagram for system configuration of role and location mapping.

FIG. 8 depicts a data flow diagram 800 for system configuration of role and location mapping. The data flow diagram 800 provides further detail for certain examples of block 702 of the example process 700 described above. At block 802, configuration begins. At block 804, a role is selected. For example, a role 805 (e.g., Administrator, Nurse, Biomedical Engineer, Pharmacist, Pharmacy Technician, Business Analyst, etc.) is selected from a plurality of options and/or specified to the domain controller 404 and/or data management system 402. Block 804 can be repeated for a plurality of roles.

Figure 9A:
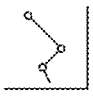
Figure 9B:
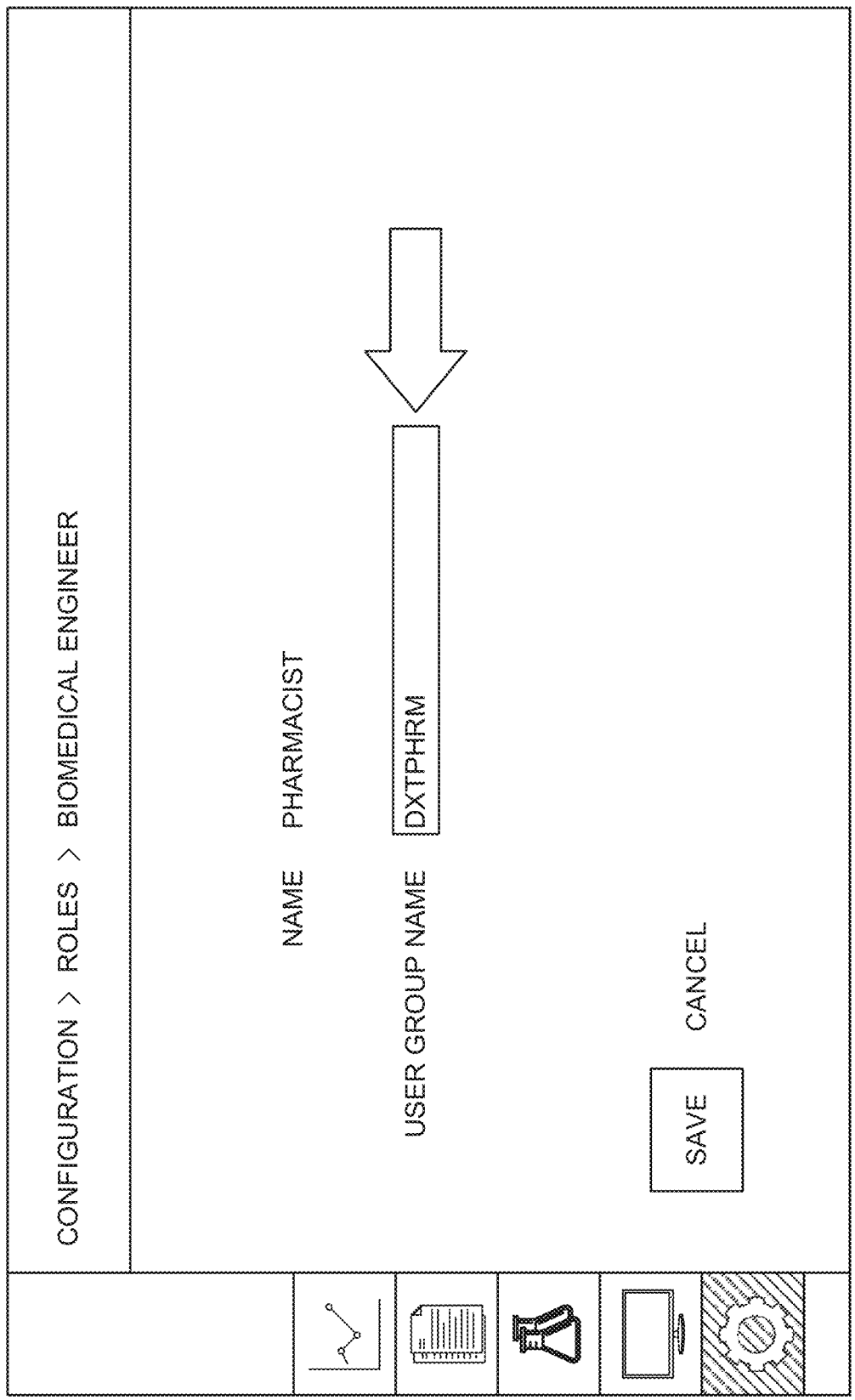

At block 806 a user group is configured for the role 805. For example, FIG. 9A illustrates an example user interface 900 to configure a user group name (e.g., DXTBMED) for a biomedical engineer role 805, and FIG. 9B illustrates an example user interface 950 to configure a user group name (e.g., DXTPHRM) for a pharmacist role 805. An example interface such as interface 970 of FIG. 9C displays the configured user group name(s) 807 for the role(s) 805. The group 807 information is used to form a role mapping 428.

Figure 10A:
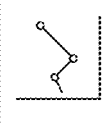
Figure 10C:
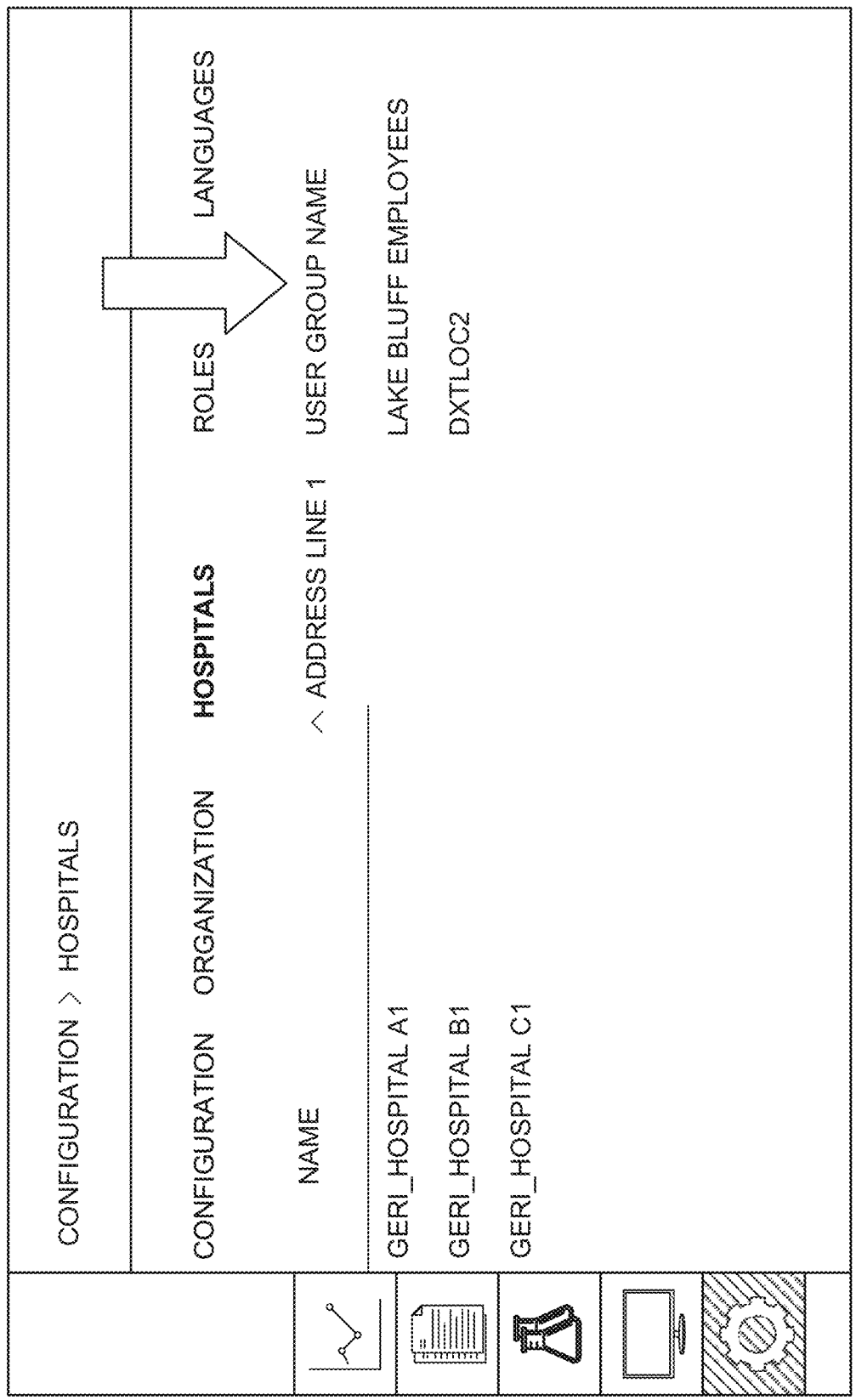

At block 810, a hospital and/or other health location is selected. For example, a hospital 811 is selected from a plurality of options and/or specified to the domain controller 404 and/or data management system 402. Block 810 can be repeated for a plurality of hospitals. At block 812, a user group name is configured for the hospital 811 (e.g., Geri Hospital A1). Block 812 can be repeated for additional hospital(s) (e.g., Geri Hospital B1, etc.). For example, FIG. 10A illustrates an example user interface 1000 to configure a user group name (e.g., Geri_Hospital A1) for a first hospital location, and FIG. 10B illustrates an example user interface 1050 to configure a user group name (e.g., Geri_Hospital B1) for a second hospital location. An example interface such as interface 1070 of FIG. 10C displays the configured user group name(s) 813 for the hospital(s) 811. The group 813 information is used to form a location mapping 524. The location mapping 524 can be combined with the role mapping 428 to form a location and role mapping for one or more users, for example.

Figure 11:
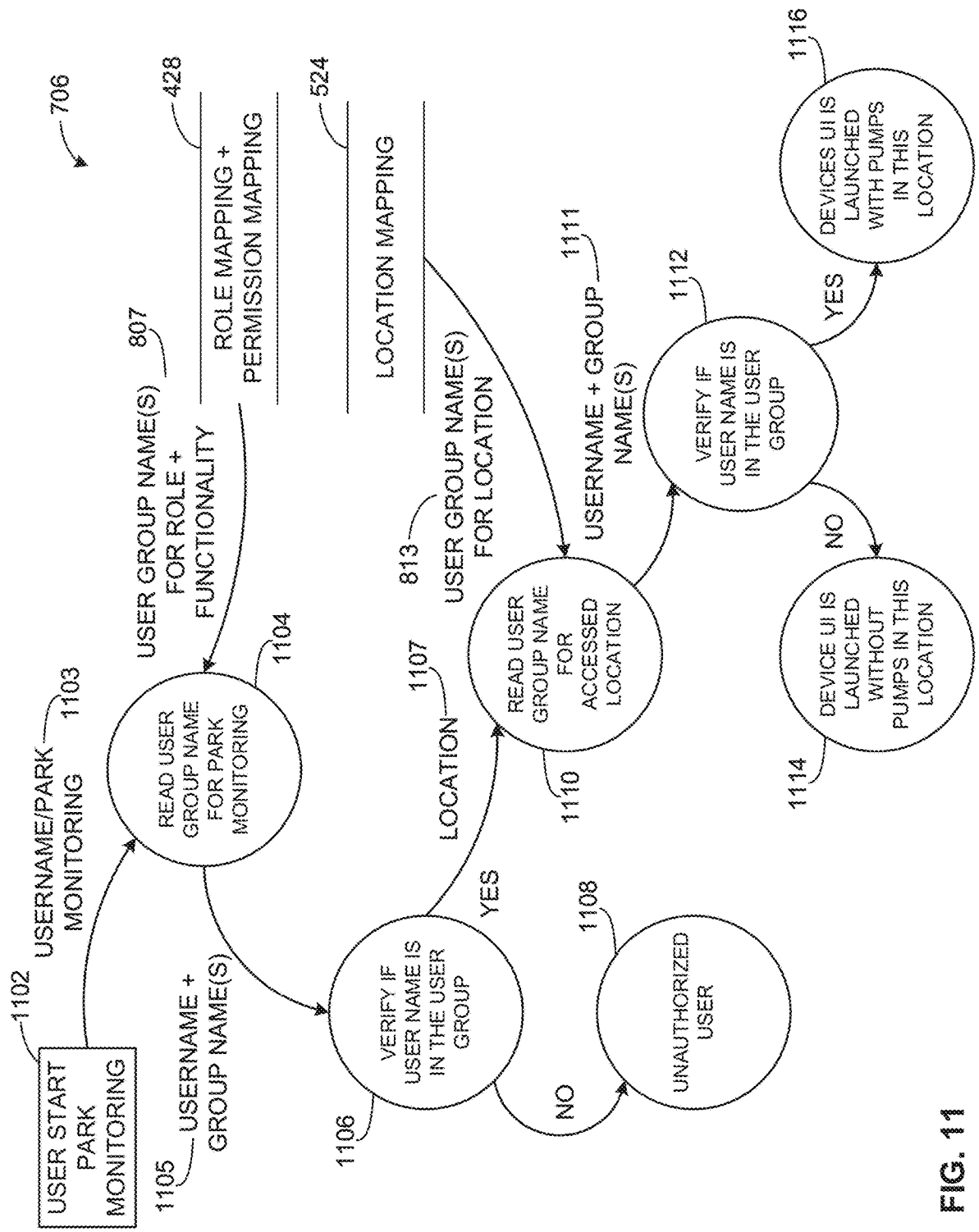
FIG. 11 depicts a data flow diagram for location authorization of a user with respect to a medical device at a location.

FIG. 11 depicts a data flow diagram 1100 for location authorization of a user with respect to a medical device at a location. The data flow diagram 1100 provides further detail for certain examples of block 706 of the example process 700 described above. At block 1102, monitoring begins. A user name 1103 is provided. For example, the user name 1103 can be input, retrieved from a database, scanned from a barcode, radio frequency identifier (RFID), determined from a photograph, etc. At block 1104, the user group name is read for monitoring. For example, based on the user name 1103 and a user group name 807 retrieved from the role mapping with user group permissions 428, a user group name is provided and combined with the user name 1105 for verification.

At block 1106, the user name is evaluated with respect to the identified user group to verify whether the user name is in the user group. For example, the user name 1103 is combined to a list associated with the user group 807 to determine whether or not the user is in the specified group. If the user name is not found in the user group, then, at block 1108, the user is labeled as an unauthorized user. If the user is labeled as an unauthorized user, the user may be blocked from accessing the system, may be flagged or reported, may be warned, may be prompted to enter different and/or additional information, etc.

However, if the user name 1103 is verified as a member of the user group 807, then a location of desired user access 1107 is provided and, at block 1110, the user group name 807 is read for the accessed location 1107. The user group name 807 and location 1107 are combined with user group name(s) for location 813 provided by the location mapping 524. Then, at block 1112, the user name and group name(s) 1111 for the location 1107 are verified to determine whether the user name is in the user group for the location.

If the user name is not found in the user group, then, at block 1114, a device interface is launched without including medical device(s) (e.g., pump(s), apheresis device(s), etc.) in the location 1107. However, if the user name is authenticated as being in the user group, then, at block 1116, a device user interface is launched which includes medical device(s) (e.g., pump(s), apheresis device(s), etc.) at the location 1107.

Figure 12A:
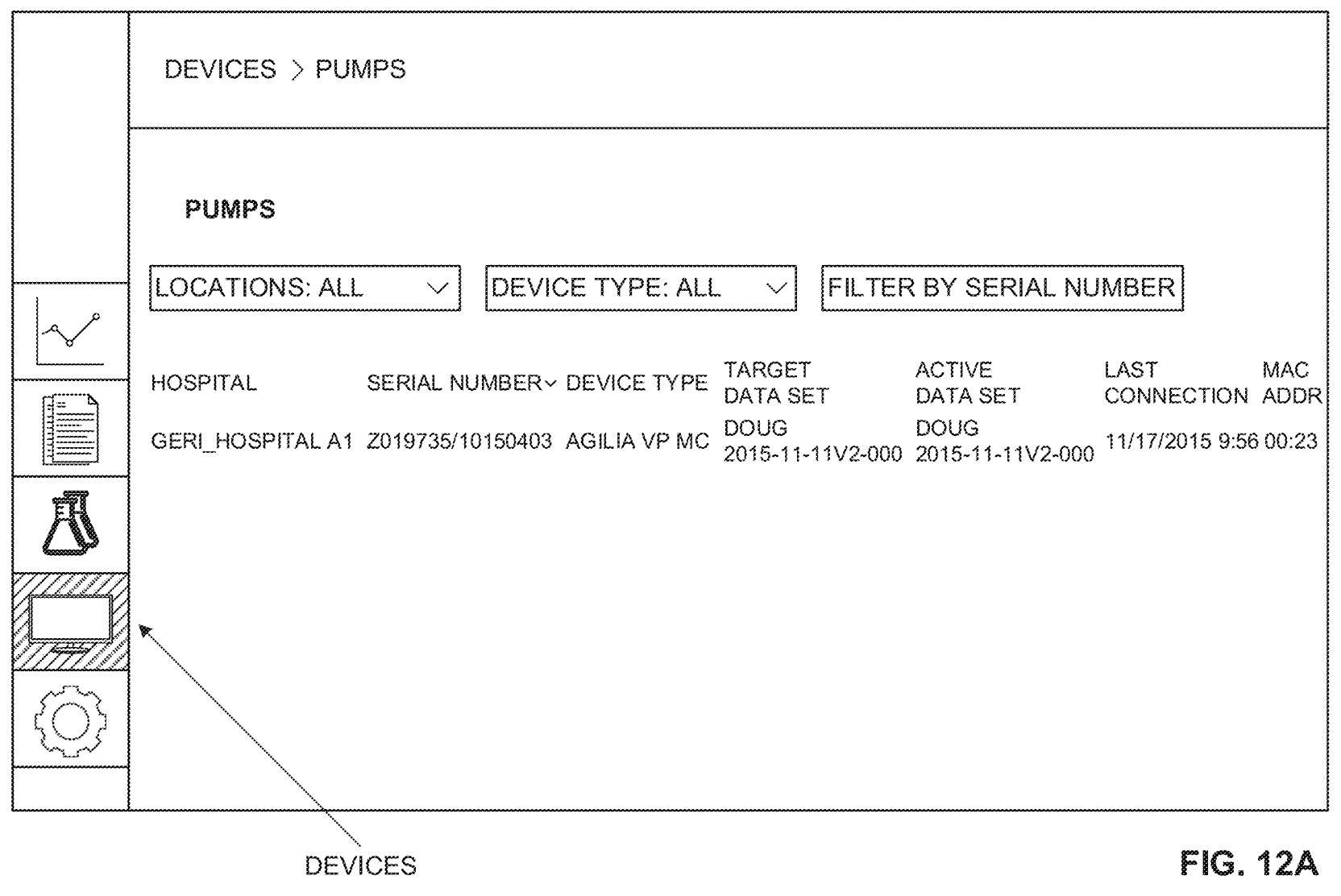

For example, a biomedical engineer configured in the Geri_Hospital A1 has proper permissions to monitor pumps in the Geri_Hospital A1 hospital. FIG. 12A illustrates an example user interface 1200 including pumps for which the biomedical engineer has authorization to monitor at the Geri_Hospital A1. The biomedical engineer launches DXT UI 1200 and then selects Devices from the Navigational panel on the left. The example user interface 1200 shows the pump in the Geri_Hospital A1 hospital, but the pumps in other hospitals are not shown on the screen 1200.

FIG. 12B illustrates an example user interface 1250 including pumps for which an administrator has authorization to monitor in the Geri_Org1 organization. An administrator configured in the Geri_Org1 organization has the permissions to monitor all pumps in the organization, so the example interface 1250 shows all three pumps in the organization and their locations (e.g., Geri_Hospital A1, Geri_Hospital B1, and Geri_Hospital C1). The administrator launches DXT UI 1250 then selects Devices from the Navigational panel on the left. The example user interface 1250 shows the pumps in all hospitals in the Geri_Org1 organization.

Figure 13:
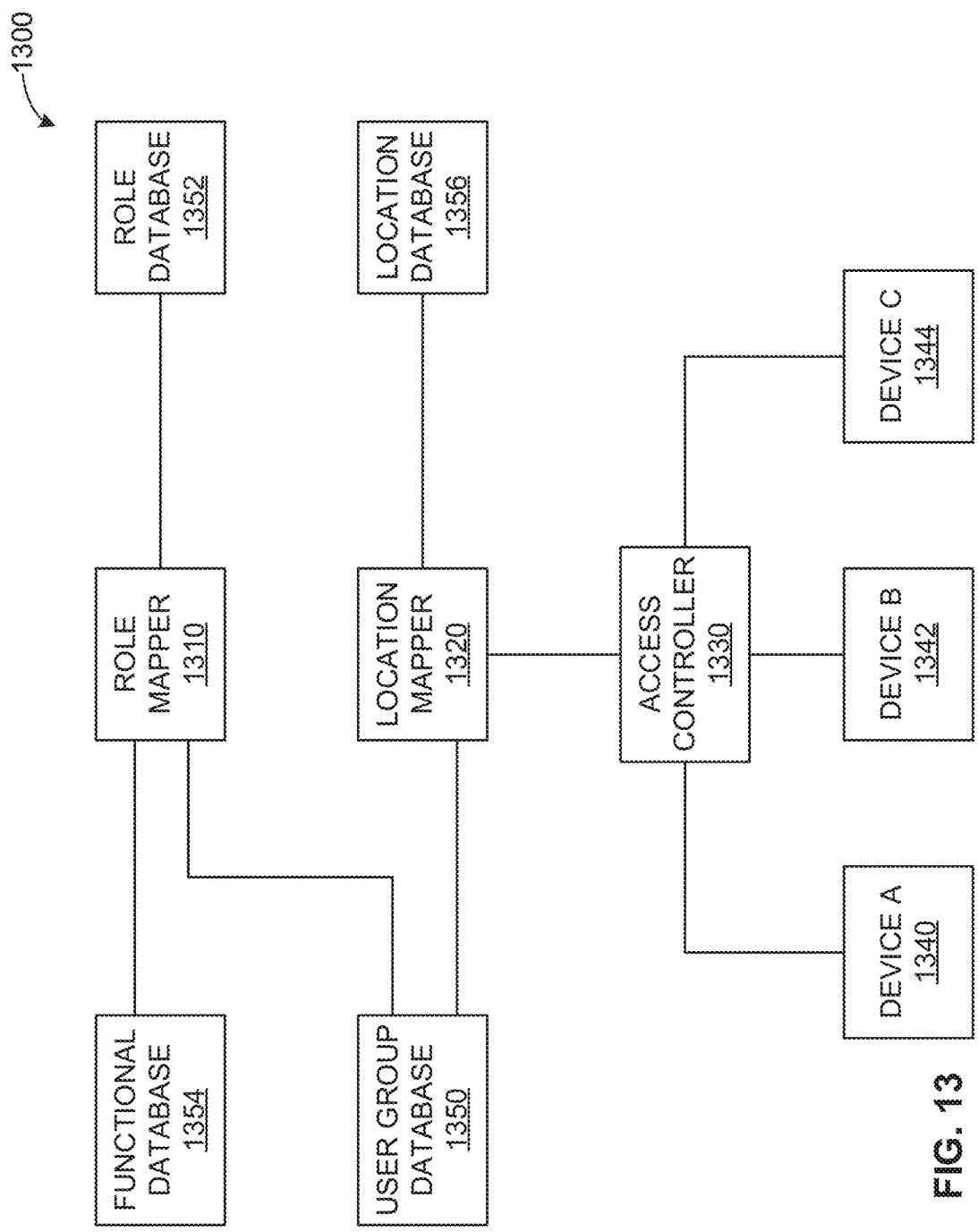
FIG. 13 is a block diagram of an example medical device monitoring and control system.

FIG. 13 is a block diagram of an example medical device monitoring and control system 1300. The example system 1300 includes a role mapper 1310, a location mapper 1320, and an access controller 1330 communicating with one or more medical devices 1340-1344. The example system 1300 can be implemented in accordance with the systems and methods described above with respect to FIGS. 1-12B, for example.

The example role mapper 1310 uses user group information from a user group database 1350 in conjunction with role information from a role database 1352 and maps user(s)/group(s) to role(s). Additionally, the role mapper 1310 uses information from a functionality database 1354 to determine what device 1340-1344 is available to which role and, therefore, to which user(s)/user group(s).

The example location mapper 1320 uses user group information from the user group database 1350 in conjunction with location information from a location database 1356 and maps user(s)/group(s) to location(s).

The access controller 1330 takes role mapping information from the role mapper 1320 and location mapping information from the location mapper 1320 to generate a role and location mapping configuration controlling which user(s) and/or user group(s) have access to which functionality for one or more medical devices 1340-1344 at one or more locations. As described in more detail above with respect to FIGS. 1-12A, the access controller 1330 restricts and/or permits information and functionality displayed on a user interface associated with one or more medical devices 1340-1344 and can customize display and device interaction for a user, for example.

Figure 14:
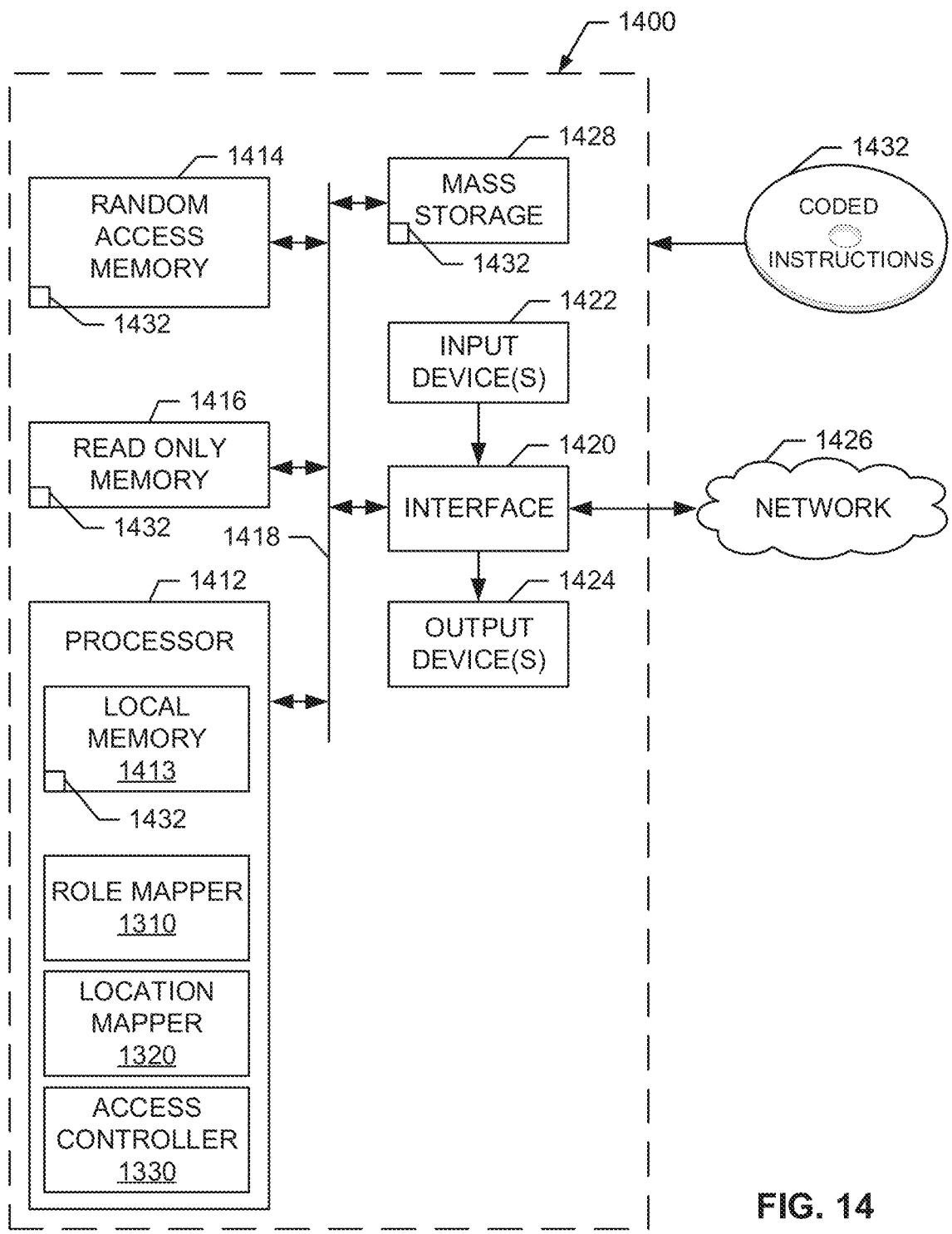
FIG. 14 is a block diagram of an example processor system that can be used to pump, implement, control and/or drive the systems and methods described herein.

FIG. 14 is a block diagram of an example processor platform 1400 capable of executing the instructions of FIGS. 7-8, and 11 to implement the example systems and interfaces of FIGS. 1-6, 9A-9C, 10A-10C, 12A-12B, and 13. The processor platform 1400 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 1400 of the illustrated example includes a processor 1412. The processor 1412 of the illustrated example is hardware. For example, the processor 1412 can be implemented by one or more integrated circuits, logic circuits, microprocessors or controllers from any desired family or manufacturer. In the illustrated example, the processor 1412 is structured to include the example role mapper 1310, the example location mapper 1320, and the example access controller 1330 of the example system 1300.

The processor 1412 of the illustrated example includes a local memory 1413 (e.g., a cache). The processor 1412 of the illustrated example is in communication with a main memory including a volatile memory 1414 and a non-volatile memory 1416 via a bus 1418. The volatile memory 1414 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1416 may be implemented by flash memory and/or any other desired type of memory device. Access to the main memory 1414, 1416 is controlled by a memory controller.

The processor platform 1400 of the illustrated example also includes an interface circuit 1420. The interface circuit 1420 may be implemented by any type of interface standard, such as an Ethernet interface, a universal serial bus (USB), and/or a PCI express interface.

In the illustrated example, one or more input devices 1422 are connected to the interface circuit 1420. The input device(s) 1422 permit(s) a user to enter data and commands into the processor 1412. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1424 are also connected to the interface circuit 1420 of the illustrated example. The output devices 1424 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1420 of the illustrated example, thus, typically includes a graphics driver card, a graphics driver chip or a graphics driver processor.

The interface circuit 1420 of the illustrated example also includes a communication device such as a transmitter, a receiver, a transceiver, a modem and/or network interface card to facilitate exchange of data with external machines (e.g., computing devices of any kind) via a network 1426 (e.g., an Ethernet connection, a digital subscriber line (DSL), a telephone line, coaxial cable, a cellular telephone system, etc.).

The processor platform 1400 of the illustrated example also includes one or more mass storage devices 1428 for storing software and/or data. Examples of such mass storage devices 1428 include floppy disk drives, hard drive disks, compact disk drives, Blu-ray disk drives, RAID systems, and digital versatile disk (DVD) drives.

Coded instructions 1432 representing the flow diagrams of FIGS. 7-8, and 11 may be stored in the mass storage device 1428, in the volatile memory 1414, in the non-volatile memory 1416, and/or on a removable tangible computer readable storage medium such as a CD or DVD.

From the foregoing, it will be appreciated that examples have been disclosed which allow access to, configure of, and control of one or more medical devices to vary automatically based on user, group, role, and/or location. Such access control can be dynamically and/or automatically determined. Access control information can be used to generate and/or otherwise customize medical device user interfaces for particular user(s) and/or group(s) of user(s) based on role, location, etc.

Certain examples facilitate determination of employee group membership. User decides what group the person belongs to. In certain examples, personnel roles are configured to map to organizational structure, which is mapped to enable and/or disable access to hardware, software, firmware, and/or other resources. Using such mapping, each person can be analyzed according to his or her role and organizational structure. Using external active directory system and domain control provides flexibility to organize users in an organization regardless of application. Rather than creating a special group with certain users or embedded users and access in a directory in the application itself, a mapping can be provided between role and group without creating a new role and/or new group and without affecting the active directory system to move users around. In certain examples, roles and groups can be created separately and linked dynamically. For example, an application provider can define a biomedical engineering role, and a hospital can define a biomedical engineering group. The hospital's installation and active directory system can map the role to the group dynamically. Access is determined based on the linkage, and the medical device data management system then determines what functionality is and is not available to the user(s) identified as biomedical engineering (e.g., by communicating from the medical device data management system to the active directory and connected devices using the Windows™ .NET API, etc.).

Certain examples provide computer-implemented methods for medical device management. An example method includes determining, using at least one processor, a role mapping for a user based on a user account including a user role and functionality available to the user role; determining, using the at least one processor, a location mapping for the user based on the user account and a location available to the user account; generating, using the at least one processor, a combined location and role mapping for the user based on the role mapping and the location mapping, the combined location and role mapping providing allowed functionality at an allowed location for the user; configuring, using the at least one processor, user access to one or more medical devices based on the combined location and role mapping; and facilitating, using the at least one processor, interaction with the one or more medical devices according to the configured user access.

In certain examples, configuring user access further includes generating a user interface for the one or more medical devices based on the combined location and role mapping for the user. In certain examples, the one or more medical devices include one or more drug delivery devices. In certain examples, the one or more drug delivery devices include one or more infusion pumps.

In certain examples, determining a role mapping includes an analysis of one or more roles with respect to the user, the one or more roles including one or more of administrator, pharmacist, or technician. In certain examples, determining a location mapping includes an analysis of one or more locations with respect to the user, the one or more locations including one or more of a region, a city, or a hospital. In certain examples, the method further includes determining one or more user groups to which the user belongs.

Certain examples provide a tangible computer readable storage medium including program code for execution by a processor. When executed, the program code is to implement a method for medical device management. The example method includes determining a role mapping for a user based on a user account including a user role and functionality available to the user role; determining a location mapping for the user based on the user account and a location available to the user account; generating a combined location and role mapping for the user based on the role mapping and the location mapping, the combined location and role mapping providing allowed functionality at an allowed location for the user; configuring user access to one or more medical devices based on the combined location and role mapping; and facilitating interaction with the one or more medical devices according to the configured user access.

In certain examples, configuring user access further includes generating a user interface for the one or more medical devices based on the combined location and role mapping for the user. In certain examples, the one or more medical devices include one or more drug delivery devices. In certain examples, the one or more drug delivery devices include one or more infusion pumps.

In certain examples, determining a role mapping includes an analysis of one or more roles with respect to the user, the one or more roles including one or more of administrator, pharmacist, or technician. In certain examples, determining a location mapping includes an analysis of one or more locations with respect to the user, the one or more locations including one or more of a region, a city, or a hospital.

Certain examples provide a system including a processor and a memory. The example processor and memory are particularly configured to implement at least a role mapper, a location mapper, and an access controller. The example role mapper is configured to determine a role mapping for a user based on a user account including a user role and functionality available to the user role. The example location mapper is configured to determine a location mapping for the user based on the user account and a location available to the user account. The example access controller is configured to: generate a combined location and role mapping for the user based on the role mapping and the location mapping, the combined location and role mapping providing allowed functionality at an allowed location for the user; configure user access to one or more medical devices based on the combined location and role mapping; and facilitate interaction with the one or more medical devices according to the configured user access.

In certain examples, configuring user access further includes generating a user interface for the one or more medical devices based on the combined location and role mapping for the user. In certain examples, the one or more medical devices include one or more drug delivery devices. In certain examples, the one or more drug delivery devices include one or more infusion pumps.

In certain examples, determining a role mapping includes an analysis of one or more roles with respect to the user, the one or more roles including one or more of administrator, pharmacist, or technician. In certain examples, determining a location mapping includes an analysis of one or more locations with respect to the user, the one or more locations including one or more of a region, a city, or a hospital. In certain examples, the user belongs to one or more user groups.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent. While particular embodiments of the invention have been shown and described, it will be obvious to those skilled in the art that changes and modifications may be made therein without departing from the invention in its broader aspects.

The invention claimed is:

1. A computer readable storage device comprising instructions that, when executed, cause a processor to at least:
launch a first user interface to configure a first user group to have access to a medical device based on a first role, the first user interface to generate a first display field to display the first role and a first input field to receive a first user group name to identify the first role, the first user group to be configured based on a first association between the first user group name and the first role, the first role to have first functionality associated with the access to the medical device;
generate a role mapping after a first configuration of the first user group based on the first association, the role mapping corresponding to a first relationship between (1) the first user group and (2) the first functionality;
launch a second user interface to configure the first user group based on a first deployment location associated with the medical device, the second user interface to generate a second display field to display the first deployment location and a second input field to receive a second user group name to identify the first deployment location, the first user group to be configured based on a second association between the second user group name and the first deployment location, the first deployment location representative of a plurality of medical devices at the first deployment location, the plurality of the medical devices including the medical device;
generate a location mapping after a second configuration of the first user group based on the second association, the location mapping corresponding to a second relationship between (1) the first user group and (2) the first deployment location;
generate a combined location and role mapping based on the role mapping and the location mapping, the combined location and role mapping to identify allowed functionality of a first user account having the first role and the first deployment location; and
launch a third user interface to facilitate interaction of the first user account with the medical device after a first determination of whether the first user account is authorized to access the medical device at the first deployment location based on the combined location and role mapping, the third user interface to:
generate a first drop-down menu including a plurality of medical device types to which the first user account has access, the plurality of the medical device types to include a medical device type of the medical device after a second determination that the first user account is authorized to access the medical device having the medical device type; and
generate a second drop-down menu including a plurality of deployment locations to which the first user account has access, the plurality of the deployment locations to include the first deployment location after a third determination that the first user account is authorized to access the medical device at the first deployment location, the third user interface to facilitate the interaction with the first drop-down menu and the second drop-down menu.

2. The computer readable storage device of claim 1, wherein the instructions, when executed, cause the processor to:
launch a fourth user interface after a third configuration of the first user group to have the access to the medical device based on a first role, the fourth user interface to:
generate a first listing of a plurality of roles including the first role; and
generate a second listing including a plurality of user group names including the first user group name, one or more of the plurality of user group names to correspond to a respective one of the plurality of roles.

3. The computer readable storage device of claim 1, wherein the instructions, when executed, cause the processor to generate a navigation bar including at least one of a configuration section, an organization section, a hospitals section, a roles section, and a languages section, the second user interface launched after a selection of the hospitals section.

4. The computer readable storage device of claim 1, wherein a plurality of user accounts having respective user names are associated with the first user group name, the plurality of user accounts include the first user account having a first user name, and the instructions, when executed, cause the processor to:
execute a first mapping of the first user name to the first user group name based on the role mapping; and
launch a fourth user interface to identify the first user name as an unauthorized user in response to the first user name not matching one of the user names associated with the first user group name, the fourth user interface to block the first user name from access the medical device by not including information associated with the medical device in the fourth user interface.

5. The computer readable storage device of claim 1, wherein a plurality of first user accounts are associated with the first user group name and a plurality of second user accounts are associated with the second user group name, the first user account having a first user name, and the instructions, when executed, cause the processor to:
execute a first mapping of the first user name to one or more second user names associated with the first user group name based on the role mapping;
execute a second mapping of the first user name to one or more third user names associated with the second user group name based on the location mapping, the second mapping in response to the first user name matching one of the one or more second user names; and
launch a fourth user interface to include first information associated with the medical device and second information associated with the first deployment location, the fourth user interface launched in response to the first user name matching one of the one or more third user names.

6. The computer readable storage device of claim 1, wherein the instructions, when executed, cause the processor to:
display one or more medical devices for one or more wards for one or more medical facilities based on the combined location and role mapping for the first user account in the third user interface, the one or more medical devices to include the medical device, the one or more medical facilities to include the first deployment location; and
display first information and second information in the third user interface, the first information including an identifier of the first deployment location, the second information including at least one of one or more respective serial numbers, one or more respective device types, one or more respective target data sets, one or more respective active data sets, respective connection information, or one or more respective media access control identifiers for the one or more medical devices.

7. The computer readable storage device of claim 1, wherein the medical device is an infusion pump, and the instructions, when executed, cause the processor to:
launch the third user interface to prevent the first user account from performing an action on the infusion pump not available to the first user account after a fourth determination that the first user account is not authorized based on the combined location and role mapping; and
launch the third user interface to enable the first user account to perform the action on the infusion pump available to the first user account after authorization of the first user account based on the combined location and role mapping, the combined location and role mapping determinative of whether the infusion pump is associated with the first user account.

8. An apparatus comprising:
memory;
machine-readable instructions; and
a processor to execute the machine-readable instructions to at least:
launch a first user interface to configure a first user group to have access to a medical device based on a first role, the first user interface to generate a first display field to display the first role and a first input field to receive a first user group name to identify the first role, the first user group to be configured based on a first association between the first user group name and the first role, the first role to have first functionality associated with the access to the medical device;
generate a role mapping in response to configuring the first user group based on the first association, the role mapping corresponding to a first relationship between (1) the first user group and (2) the first functionality;
launch a second user interface to configure the first user group based on a first deployment location associated with the medical device, the second user interface to generate a second display field to display the first deployment location and a second input field to receive a second user group name to identify the first deployment location, the first user group to be configured based on a second association between the second user group name and the first deployment location, the first deployment location representative of a plurality of medical devices at the first deployment location, the plurality of the medical devices including the medical device;
generate a location mapping in response to configuring the first user group based on the second association, the location mapping corresponding to a second relationship between (1) the first user group and (2) the first deployment location;
generate a combined location and role mapping based on the role mapping and the location mapping, the combined location and role mapping to identify allowed functionality of a first user account having the first role and the first deployment location; and
launch a third user interface to facilitate interaction of the first user account with the medical device in response to determining whether the first user account is authorized to access the medical device at the first deployment location based on the combined location and role mapping, the third user interface to:
generate a first drop-down menu including a plurality of medical device types to which the first user account has access, the plurality of the medical device types to include a medical device type of the medical device in response to a first determination that the first user account is authorized to access the medical device having the medical device type; and
generate a second drop-down menu including a plurality of deployment locations to which the first user account has access, the plurality of the deployment locations to include the first deployment location in response to a second determination that the first user account is authorized to access the medical device at the first deployment location, the third user interface to facilitate the interaction with the first drop-down menu and the second drop-down menu.

9. The apparatus of claim 8, wherein the processor is to:
launch a fourth user interface in response to configuring the first user group to have the access to the medical device based on a first role, the fourth user interface to:
generate a first listing of a plurality of roles including the first role; and
generate a second listing including a plurality of user group names including the first user group name, one or more of the plurality of user group names to correspond to a respective one of the plurality of roles.

10. The apparatus of claim 8, wherein the processor is to generate a navigation bar including at least one of a configuration section, an organization section, a hospitals section, a roles section, and a languages section, the second user interface launched in response to a selection of the hospitals section.

11. The apparatus of claim 8, wherein a plurality of user accounts having respective user names are associated with the first user group name, the plurality of user accounts include the first user account having a first user name, and the processor is to:
execute a first mapping of the first user name to the first user group name based on the role mapping; and
launch a fourth user interface to identify the first user name as an unauthorized user in response to the first user name not matching one of the user names associated with the first user group name, the fourth user interface to block the first user name from access the medical device by not including information associated with the medical device in the fourth user interface.

12. The apparatus of claim 8, wherein a plurality of first user accounts are associated with the first user group name and a plurality of second user accounts are associated with the second user group name, the first user account having a first user name, and the processor is to:
execute a first mapping of the first user name to one or more second user names associated with the first user group name based on the role mapping;
execute a second mapping of the first user name to one or more third user names associated with the second user group name based on the location mapping, the second mapping in response to the first user name matching one of the one or more second user names; and
launch a fourth user interface to include first information associated with the medical device and second information associated with the first deployment location, the fourth user interface launched in response to the first user name matching one of the one or more third user names.

13. The apparatus of claim 8, wherein the processor is to:
display one or more medical devices for one or more wards for one or more medical facilities based on the combined location and role mapping for the first user account in the third user interface, the one or more medical devices to include the medical device, the one or more medical facilities to include the first deployment location; and
display first information and second information in the third user interface, the first information including an identifier of the first deployment location, the second information including at least one of one or more respective serial numbers, one or more respective device types, one or more respective target data sets, one or more respective active data sets, respective connection information, or one or more respective media access control identifiers for the one or more medical devices.

14. The apparatus of claim 8, wherein the medical device is an infusion pump, and the processor is to:
launch the third user interface to prevent the first user account from performing an action on the infusion pump not available to the first user account in response to not authorizing the first user account based on the combined location and role mapping; and
launch the third user interface to enable the first user account to perform the action on the infusion pump available to the first user account in response to authorizing the first user account based on the combined location and role mapping, the combined location and role mapping determinative of whether the infusion pump is associated with the first user account.

15. A method comprising:
launching, by executing an instruction with a processor, a first user interface to configure a first user group to have access to a medical device based on a first role, the first user interface to generate a first display field to display the first role and a first input field to receive a first user group name to identify the first role, the first user group to be configured based on a first association between the first user group name and the first role, the first role to have first functionality associated with the access to the medical device;
generating, by executing an instruction with the processor, a role mapping in response to configuring the first user group based on the first association, the role mapping corresponding to a first relationship between (1) the first user group and (2) the first functionality;
launching, by executing an instruction with the processor, a second user interface to configure the first user group based on a first deployment location associated with the medical device, the second user interface to generate a second display field to display the first deployment location and a second input field to receive a second user group name to identify the first deployment location, the first user group to be configured based on a second association between the second user group name and the first deployment location, the first deployment location representative of a plurality of medical devices at the first deployment location, the plurality of the medical devices including the medical device;
generating, by executing an instruction with the processor, a location mapping in response to configuring the first user group based on the second association, the location mapping corresponding to a second relationship between (1) the first user group and (2) the first deployment location;
generating, by executing an instruction with the processor, a combined location and role mapping based on the role mapping and the location mapping, the combined location and role mapping to identify allowed functionality of a first user account having the first role and the first deployment location; and
launching, by executing an instruction with the processor, a third user interface to facilitate interaction of the first user account with the medical device in response to determining whether the first user account is authorized to access the medical device at the first deployment location based on the combined location and role mapping, the third user interface to:
generate a first drop-down menu including a plurality of medical device types to which the first user account has access, the plurality of the medical device types to include a medical device type of the medical device in response to a first determination that the first user account is authorized to access the medical device having the medical device type; and
generate a second drop-down menu including a plurality of deployment locations to which the first user account has access, the plurality of the deployment locations to include the first deployment location in response to a second determination that the first user account is authorized to access the medical device at the first deployment location, the third user interface to facilitate the interaction with the first drop-down menu and the second drop-down menu.

16. The method of claim 15, further including:
launching a fourth user interface in response to configuring the first user group to have the access to the medical device based on a first role, the fourth user interface to:
generate a first listing of a plurality of roles including the first role; and
generate a second listing including a plurality of user group names including the first user group name, one or more of the plurality of user group names to correspond to a respective one of the plurality of roles.

17. The method of claim 15, wherein a plurality of user accounts having respective user names are associated with the first user group name, the plurality of user accounts include the first user account having a first user name, and further including:
executing a first mapping of the first user name to the first user group name based on the role mapping; and
launching a fourth user interface to identify the first user name as an unauthorized user in response to the first user name not matching one of the user names associated with the first user group name, the fourth user interface to block the first user name from access the medical device by not including information associated with the medical device in the fourth user interface.

18. The method of claim 15, wherein a plurality of first user accounts are associated with the first user group name and a plurality of second user accounts are associated with the second user group name, the first user account having a first user name, and further including:
executing a first mapping of the first user name to one or more second user names associated with the first user group name based on the role mapping;

executing a second mapping of the first user name to one or more third user names associated with the second user group name based on the location mapping, the second mapping in response to the first user name matching one of the one or more second user names; and launching a fourth user interface to include first information associated with the medical device and second information associated with the first deployment location, the fourth user interface launched in response to the first user name matching one of the one or more third user names.

19. The method of claim 15, further including:

displaying one or more medical devices for one or more wards for one or more medical facilities based on the combined location and role mapping for the first user account in the third user interface, the one or more medical devices to include the medical device, the one or more medical facilities to include the first deployment location; and displaying first information and second information in the third user interface, the first information including an identifier of the first deployment location, the second information including at least one of one or more respective serial numbers, one or more respective device types, one or more respective target data sets, one or more respective active data sets, respective connection information, or one or more respective media access control identifiers for the one or more medical devices.

20. The method of claim 15, wherein the medical device is an infusion pump, and further including:

launching the third user interface to prevent the first user account from performing an action on the infusion pump not available to the first user account in response to not authorizing the first user account based on the combined location and role mapping; and launching the third user interface to enable the first user account to perform the action on the infusion pump available to the first user account in response to authorizing the first user account based on the combined location and role mapping, the combined location and role mapping determinative of whether the infusion pump is associated with the first user account.

* * * * *